(12) United States Patent
Morcos et al.

(10) Patent No.: US 6,228,392 B1
(45) Date of Patent: May 8, 2001

(54) OSMOTIC DELIVERY COMPOSITION, SOLUTION, AND METHOD

(75) Inventors: Paul Anton Morcos; James Edward Summerton; James Patrick Summerton, all of Corvallis, OR (US)

(73) Assignee: Gene Tools, LLC, Corvallis, OR (US)

( * ) Notice: Subject to any disclaimer, the term of this patent is extended or adjusted under 35 U.S.C. 154(b) by 0 days.

(21) Appl. No.: 09/302,013

(22) Filed: Apr. 29, 1999

(51) Int. Cl.[7] .................................................. A61K 9/127
(52) U.S. Cl. .............................. 424/450; 935/54; 514/44
(58) Field of Search .................................... 424/400, 450, 424/94.3; 935/54; 436/826; 516/44

(56) References Cited

U.S. PATENT DOCUMENTS 5,707,648 * 1/1998 Yiu ........................................ 424/450
5,792,471 * 8/1998 Curatalo ............................... 424/480

OTHER PUBLICATIONS

BioProbes 28, p. 13. May 1998, Published by Molecular Probes, Inc., Eugene, Oregon, USA.
Chakrabarti et al., Journal of Biol. Chem. 264:8214 (1989).
Lee et al., Cytometry 14:265 (1993).
McElligott & Dice, Bioscience Reports 4:451 (1984).
Okada & Rechsteiner, Cell 29:33 (1982).
Rechsteiner, Methods in Enzymology 149:42 (1987).

* cited by examiner

Primary Examiner—Gollamudi S. Kishore
(74) Attorney, Agent, or Firm—Lori M. Friedman (57) ABSTRACT

The invention relates to a composition, solution, and method for delivering desired substances into the cytosol of living eucaryotic cells. The composition includes a poly(ethylene glycol) component having a designated molecular weight in the range between about 300 and about 900 daltons, and a carbohydrate component which is membrane impermeable and water soluble. The osmotic delivery solution delivers reporter-tagged molecules and complexes, drugs, antisense and antigene oligos, RNAs, DNAs, peptides, proteins, carbohydrates, and the like into cultured cells using an improved osmotic delivery method. The method may also be used for extracorporal therapy. In a particularly preferred embodiment of extracorporal therapy, the desired substance delivered into the cytosol of the cells is a Morpholino antisense oligo.

7 Claims, 8 Drawing Sheets

Figure 1

Postulated PEG insertion complex in lipid bilayer

Figure 2

MALDI-TOF Mass Spectrum of PEG-1000

Figure 3

Delivery as function of PEG size

Delivery as function of volumes of solution added in step 2 of Osmotic Delivery Method

OSMOTIC DELIVERY COMPOSITION, SOLUTION, AND METHOD

BACKGROUND OF THE INVENTION

1. Field of the Invention

The present invention relates to a composition and solution, as well as use of such composition and solution for delivering substances into the cytosol of living eucaryotic cells.

REFERENCES

*BioProbes* 28:13. May 1998, Pub. by Molecular Probes, Inc., Eugene, Oreg.
Chakrabarti et al., *Journal of Biol. Chem.* 264:8214 (1989).
Lee et al., *Cytometry* 14:265 (1993).
McElligott & Dice, *Bioscience Reports* 4:451 (1984).
Okada & Rechsteiner, *Cell* 29:33 (1982).
Rechsteiner, *Methods in Enzymology* 149:42 (1987).

2. Background and Prior Art

In the course of biological research and certain medical procedures it is desirable to introduce a variety of substances into the cytosol of living eucaryotic cells. However, most hydrophilic substances, including many drugs, antisense and antigene oligos, RNAs, DNAs, peptides, proteins, carbohydrates, and combinations thereof, enter eucaryotic cells primarily via endocytosis and are subsequently sequestered or degraded in lysosomes, with little of no intact substance achieving the desired entry into the cytosol of the cells.

A variety of methods have been devised to deliver hydrophilic substances directly across the cytoplasmic membrane, including: complexing such substances with or incorporating such substances within liposomes (Capaccioli et al., *Biochem. Biophys. Res. Comm.* 197:818 (1993)); contacting cells with such substances while generating transient pores in the membrane with Streptolysin O (Spiller & Tidd, *Antisense Res. & Dev.* 5:13 (1995)) or by scraping adherent cells from a surface (Partridge et al., *Antisense Nuc. Acid Drug Dev.* 6:169 (1996)), or by treating cells with an amphiphilic peptide under acidic conditions (Pichon et al., *Antisense & Nuc. Acid Drug Dev.* 7:335 (1997)); and, covalently attaching a special amphiphilic transport peptide or protein (Pooga et al., *Nature BioTech.* 16:857 (1998)) to the substance to be delivered.

In contrast to the foregoing direct-entry approaches, only a few delivery methods have been reported which exploit the natural endocytotic route into cells as the first step toward cytosolic delivery. One such indirect method was devised by Summerton and Weller (*Nucleosides & Nucleotides* 16:1785 (1997)), and entails covalent linkage of a molecular transport engine to the substance to be delivered, said engine being powered by the pH differential between the late endosome and the cytosol.

Another indirect method, which bears directly on the instant invention, is the three-solution osmotic delivery method devised by Okada & Rechsteiner (*Cell* 29:33 (1982)), which entails: 1) loading endosomes with an aqueous hypertonic solution of sucrose and poly(ethylene glycol)-1000 and the substance to be delivered; followed by, 2) exposure of the cells to a hypotonic solution to effect release of the endosomal contents into the cytosol due to osmotic pressure generated within the endosome; and, 3) replacing the hypotonic solution with isotonic solution to return the cells to their normal metabolic state. This osmotic delivery method is potentially very useful because it can routinely be used for delivering a broad range of substances into both adherent and non-adherent cells.

While this osmotic delivery method does achieve delivery of substances into the cytosol of cells, nonetheless, the method generally used heretofore (Okada & Rechsteiner, *Cell* 29:33 (1982); McElligott & Dice, *Bioscience Reports* 4:451 (1984); Rechsteiner, *Methods in Enzymology* 149:42 (1987); Lee et al., *Cytometry* 14:265 (1993); *BioProbes*, 28:13 (1998)) is complicated to use because of multiple steps with stringent time constraints. This presents difficulties when one wishes to deliver substances into multiple samples of adherent cells, or into even a single sample of non-adherent cells. Further, delivery efficiencies are less than optimal and vary significantly between cell samples. Finally, contacting the cells with the hypotonic solution often causes losses in cell viability, with such viability losses varying due to minor differences in experimental method and minor differences in time of exposure to the hypotonic solution.

A related two-solution osmotic delivery method was reported by Chakrabarti et al. (*The Journal of Biological Chemistry* 264:8214 (1989)). This prior-art two-solution osmotic delivery method suffers from various limitations, including: it affords limited delivery because of a suboptimal poly(ethylene glycol) component, a sub-optimal treatment time, and use of a less effective and cumbersome volume of solution in the second step. Further, it is of little commercial utility because the excessive volume of solution used in the second step effectively precludes its use with adherent cells and renders it inefficient and cumbersome for extracorporal therapy.

SUMMARY OF THE INVENTION

Accordingly, an object of the present invention is to provide a novel osmotic delivery composition which affords delivery of greater amounts of desired substances into the cytosol of living eucaryotic cells then prior-art osmotic delivery compositions.

Another object of the invention is to provide an osmotic delivery method utilizing the osmotic delivery composition which affords more reproducible delivery of desired substances into the cytosol of living eucaryotic cells than prior-art osmotic delivery methods.

A further object of the invention is to provide an osmotic delivery method which is simpler and easier to use with multiple samples of adherent cells and with non-adherent cells than osmotic delivery methods previously used for this purpose. This object relates to improving the efficiency of research with cultured cells and to reducing the cost and complexity of extracorporal therapies.

The invention includes an osmotic delivery composition comprising a poly(ethylene glycol) component having a designated molecular weight in the range of about 300 to about 900 daltons, and a water-soluble membrane-impermeable carbohydrate component.

In a preferred embodiment, the poly(ethylene glycol) component has a designated molecular weight of 600 and the carbohydrate component is sorbitol.

The osmotic delivery composition may further be dissolved in an aqueous medium.

The aqueous solution of the osmotic delivery composition may further include one or more substances to be delivered into the cytosol of the cells.

Also included in the invention is a method for osmotic delivery of substances into the cytosol of living eucaryotic cells, said method comprising the steps of:

a) contacting the cells with an aqueous solution of the osmotic delivery composition of the invention, which further contains the one or more substances to be delivered into the cytosol of the cells; followed by, b) adding cell culture medium.

These and other objects and features of the invention will be more fully apparent from the following detailed description of the invention and accompanying figures.

DETAILED DESCRIPTION OF THE INVENTION

PEG Component:

While a poly(ethylene glycol) component has been found to be necessary for effective cytosolic delivery by published osmotic delivery methods, no detailed mechanism has heretofore been proposed for how the poly(ethylene glycol) component contributes to cytosolic delivery.

Figure 1:
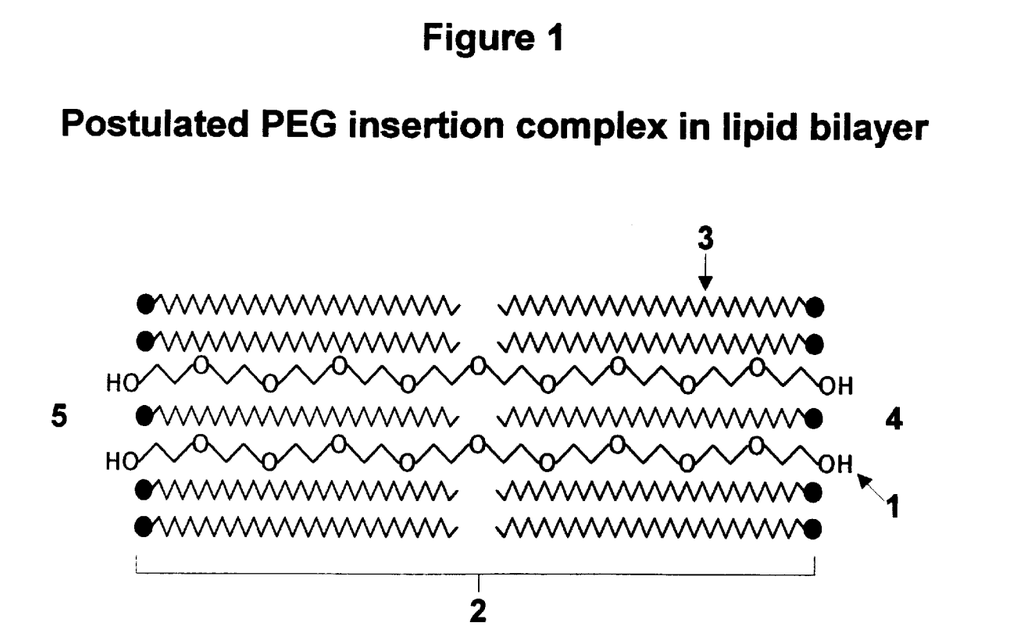
FIG. 1 is a diagram illustrating the postulated PEG insertion complex in a lipid bilayer.

After considering the properties of endosomal membranes and poly(ethylene glycol), applicants postulated that the poly(ethylene glycol) molecules form an insertion complex in the endosomal membrane, as illustrated in FIG. 1. As shown in this figure, the poly(ethylene glycol) molecules 1 insert into the lipid layer of the endosomal membrane 2 where said poly(ethylene glycol) chains exist in an extended conformation parallel with the fatty acid chains 3 of the membrane lipids. In such an insertion complex the poly (ethylene glycol) chain spans the endosomal membrane, with one hydrophilic hydroxyl terminus contacting the aqueous endosomal compartment 4 and the other hydrophilic hydroxyl terminus contacting the aqueous cytosol 5. A high concentration of such poly(ethylene glycol) chains extending through the interior of the lipid bilayer is expected to render the interior of the membrane moderately hydrophilic and thereby substantially reduce the energy cost of disrupting the hydrophobic interactions between the fatty acid chains, said interactions being largely responsible for the integrity of the membrane. Thus, the poly(ethylene glycol) is believed to render the membrane more easily disrupted by osmotic pressure which will develop when there is an influx of water into the hypertonic solution contained within the endosome of cells which have been exposed to said hypertonic solution.

The above detailed model predicts that the most effective poly(ethylene glycol) would be one which just spans the endosomal membrane. This is because poly(ethylene glycol) chains which are shorter than the thickness of the membrane are more likely to remain in the aqueous phase because of the energy cost of inserting one hydrophilic hydroxyl into the interior of the lipid bilayer. Conversely, poly(ethylene glycol) chains which are appreciably longer than the thickness of the membrane are expected to be less likely to form the postulated insertion complex because in aqueous solution they are reported to preferentially form ordered secondary structures wherein proximal ether oxygens are bridged by water molecules (Antonsen & Hoffmann, page 26 in Poly(ethylene glycol) Chemistry, Biotech. & Biomed. Applic., Ed. J. Milton Harris, Pub. Plenum Press, New York (1992)). Membrane entry of these longer poly(ethylene glycol)s having such ordered secondary structures will be disfavored due to the energy cost associated with insertion of their hydrated structures into the lipid bilayer.

In regard to this predicted most effective poly(ethylene glycol) length for cytosolic delivery, the lipid bilayer of endosomal membranes is typically about 36 A to 40 A thick in eucaryotic cells, and the repeating unit of poly(ethylene glycol) ($-CH_2-CH_2-O-$) in its extended conformation is 3.75 A. Therefore, to span the endosomal membrane the poly(ethylene glycol) should contain about 10 or 11 repeating units, ie., HO—$(CH_2-CH_2-O)_n$—H, where n=10 or 11.

Figure 2:
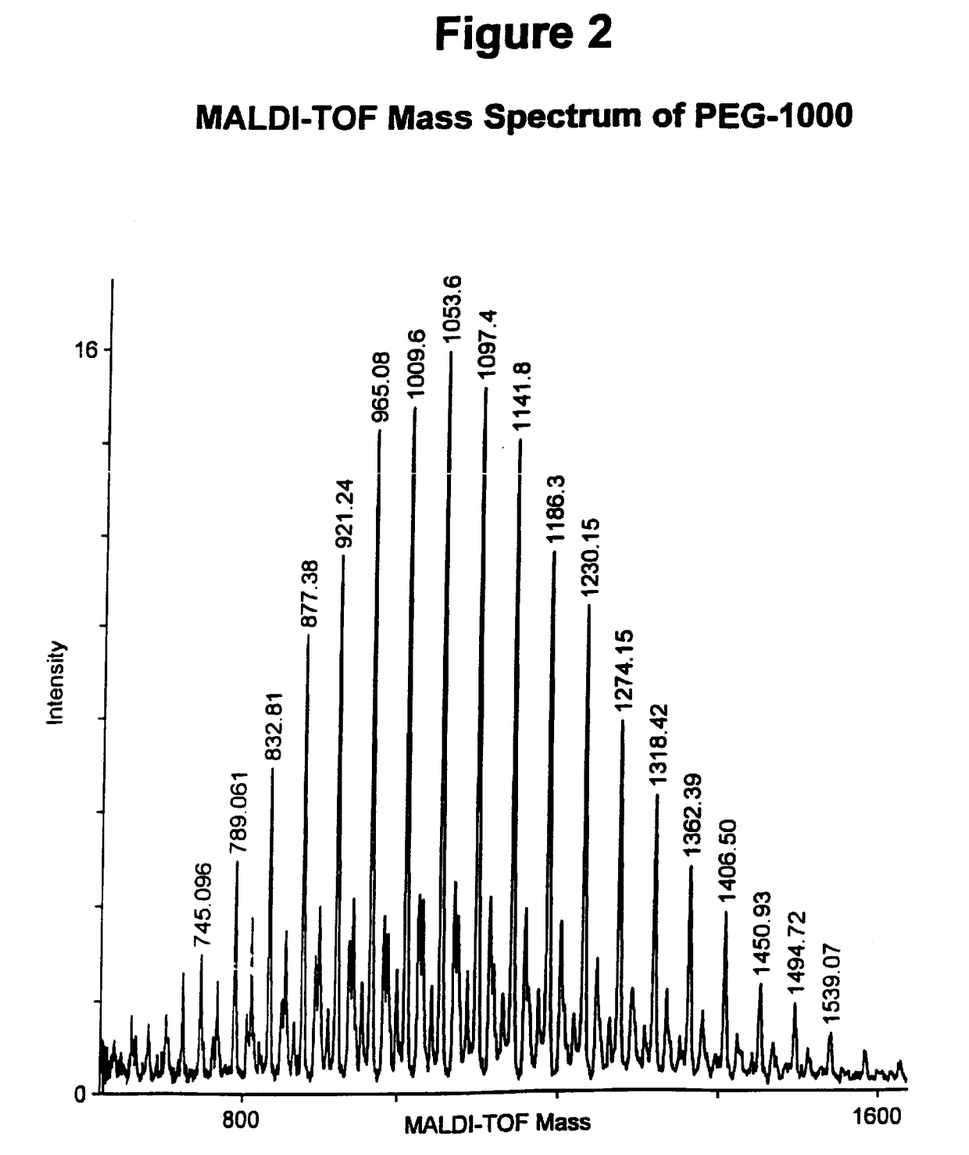
FIG. 2 is a MALDI-TOF Mass Spectrum of PEG-1000.

A poly(ethylene glycol) with 10 repeating units has a molecular weight of 459 daltons, and a poly(ethylene glycol) with 11 repeating units has a molecular weight of 503 daltons. Commercially available preparations of poly (ethylene glycol) of a designated molecular weight value comprise a composite of molecules with a range of molecular weights distributed about this designated molecular weight value. FIG. 2 shows a representative distribution of molecular weight species (each including a sodium ion used to effect ionization) of a representative poly(ethylene glycol)-1000 preparation (1000 being the designated molecular weight value) purchased from Aldrich Chemical Co., Milwaukee, Wis., and analyzed by Matrix Assisted Laser Desorption Time Of Flight mass spectroscopy.

The postulated mechanism of action of the poly(ethylene glycol) component led to the prediction that the most effective poly(ethylene glycol) preparations would be those having the highest concentrations of poly(ethylene glycol)-459 and/or poly(ethylene glycol)-503. From typical distributions of poly(ethylene glycol) molecular weights about the designated molecular weight value we concluded that the commercially-available poly(ethylene glycol) preparations in about the 300 to 900 molecular weight range should be more effective for achieving cytosolic delivery than the poly(ethylene glycol)-1000 and poly(ethylene glycol)-1500 components used in all prior-art osmotic delivery methods.

Accordingly, a series of poly(ethylene glycol)s in a molecular weight range outside of that previously utilized for prior-art osmotic delivery compositions was investigated. These non-prior-art poly(ethylene glycol) preparations included the commercially-available poly(ethylene glycol) preparations having designated molecular weights of: 200, 300, 400, 600, and 900. For comparison, poly (ethylene glycol) preparations having designated molecular weights of 1000 and 1500 used in all reported prior-art osmotic delivery methods were also tested, as well as poly(ethylene glycol 2000. The method used in these tests is detailed in Example 1. The results, shown in FIG. 3, indicate that those poly(ethylene glycol) preparations having the highest concentration of species with a length optimal for spanning the endosomal membrane (ie., poly(ethylene glycol)s having designated molecular weight values in the range of about 300 to about 900 daltons) are also the most effective in achieving cytosolic delivery by the osmotic delivery method of the instant invention—with poly (ethylene glycol)-600 affording the greatest activity.

Accordingly, the poly(ethylene glycol) component of the osmotic delivery composition of the invention, hereafter designated the "PEG Component", is selected from poly (ethylene glycol) preparations having designated molecular weight values in the range from about 300 to about 900 daltons.

Figure 3:
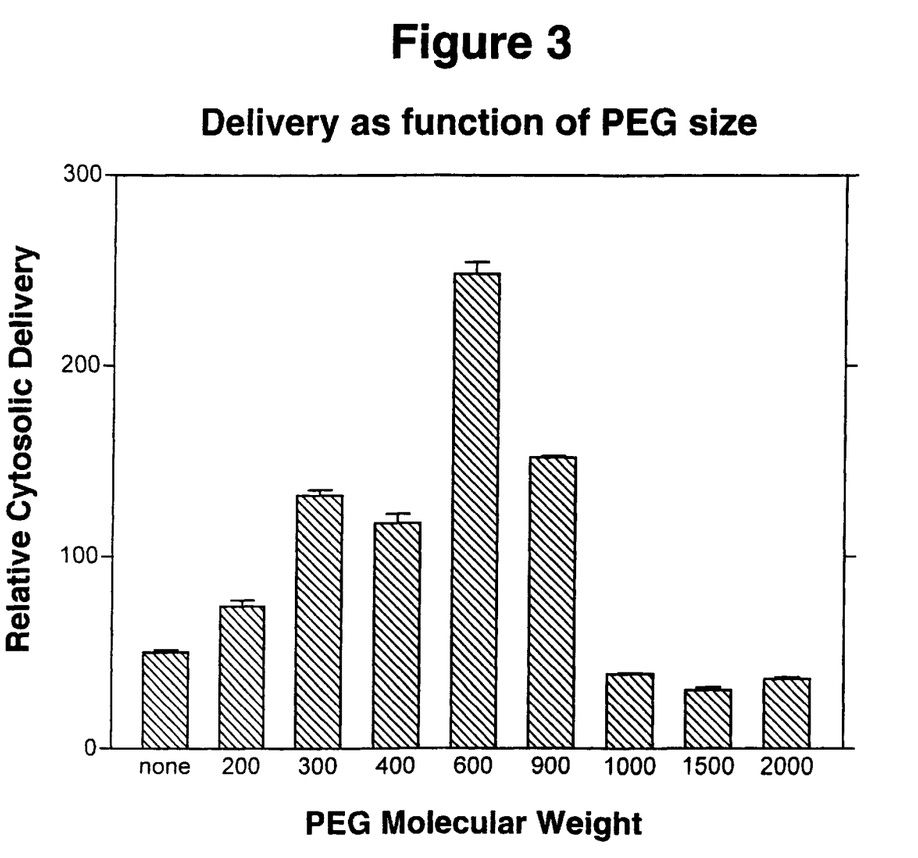
FIG. 3 is a graph showing relative cytosolic delivery as a function of the PEG size.

It is noteworthy that the poly(ethylene glycol)-1000 and poly(ethylene glycol)-1500 utilized in all prior art osmotic delivery compositions and methods are seen in FIG. 3 to be appreciably less effective in achieving cytosolic delivery than is the PEG Component of the instant invention.

Carbohydrate Component:

While the prior art osmotic delivery compositions utilize only sucrose for achieving high osmolarity, as described in Example 2 the applicants have assessed the effectiveness of a variety of carbohydrates for osmotic delivery. The results, shown in FIG. 4, suggest that high osmolarity is preferentially achieved by a carbohydrate (poly-alcohol) which satisfies the following criteria:

a) membrane-impermeable; and,
b) water-soluble.

Membrane-impermeable, as used herein, is defined as having little membrane permeability over the period of about 8 to about 25 minutes during which time the osmotic delivery method takes place. This requirement for membrane-impermeability is based on the finding, as described in Example 2 with results shown in FIG. 4, that low molecular weight alcohols, such as ethanol, ethylene glycol, and to a lesser extent, glycerol, fail to achieve good cytosolic delivery. This is believed to be because these alcohols pass through cell membranes sufficiently fast that there is inadequate buildup of osmotic pressure within endosomes to effect endosomal release of the substance to be delivered into the cytosol. Conversely, it has been found that poly-alcohols containing four or more alcohol moieties can afford good cytosolic delivery and so satisfy this membrane-impermeable requirement.

Thus, the requirement that the carbohydrate component be membrane-impermeable effectively precludes mono-, di-, and tri-alcohols (eg., ethanol, ethylene glycol, and glycerol, respectively), but includes poly-alcohols containing four or more alcohol moieties, as well as monosaccharides and disaccharides.

Water-soluble is defined in the context of this invention as being soluble in aqueous solution at a concentration of at least about 0.2 Molal, and preferably about 1.0 Molal at room temperature when normal saline or cell culture medium is used as the aqueous solvent (normal saline or cell culture medium contributes about 0.3 osmolality). Alternatively, water-solubility should be at least about 0.5 Moial for the carbohydrate component when just water is used as the aqueous solvent, since in such case the aqueous component does not contribute to the osmolality. This requirement for water-solubility is based on the finding, as described in a later section and detailed in Example 4 with results shown in FIG. 6, that effective cytosolic delivery requires that the carbohydrate component be at least this water soluble—presumably because resulting osmolalities at least this high are required to generate sufficient osmotic pressure within the endosome to effect endosomal release of the substance to be delivered into the cytosol. The requirement that the carbohydrate component have sufficient water solubility to form an aqueous solution of at least about 0.2 Molal effectively precludes relatively low-solubility carbohydrates such as the disaccharide, lactose, as well as carbohydrates larger than disaccharides.

Figure 4:
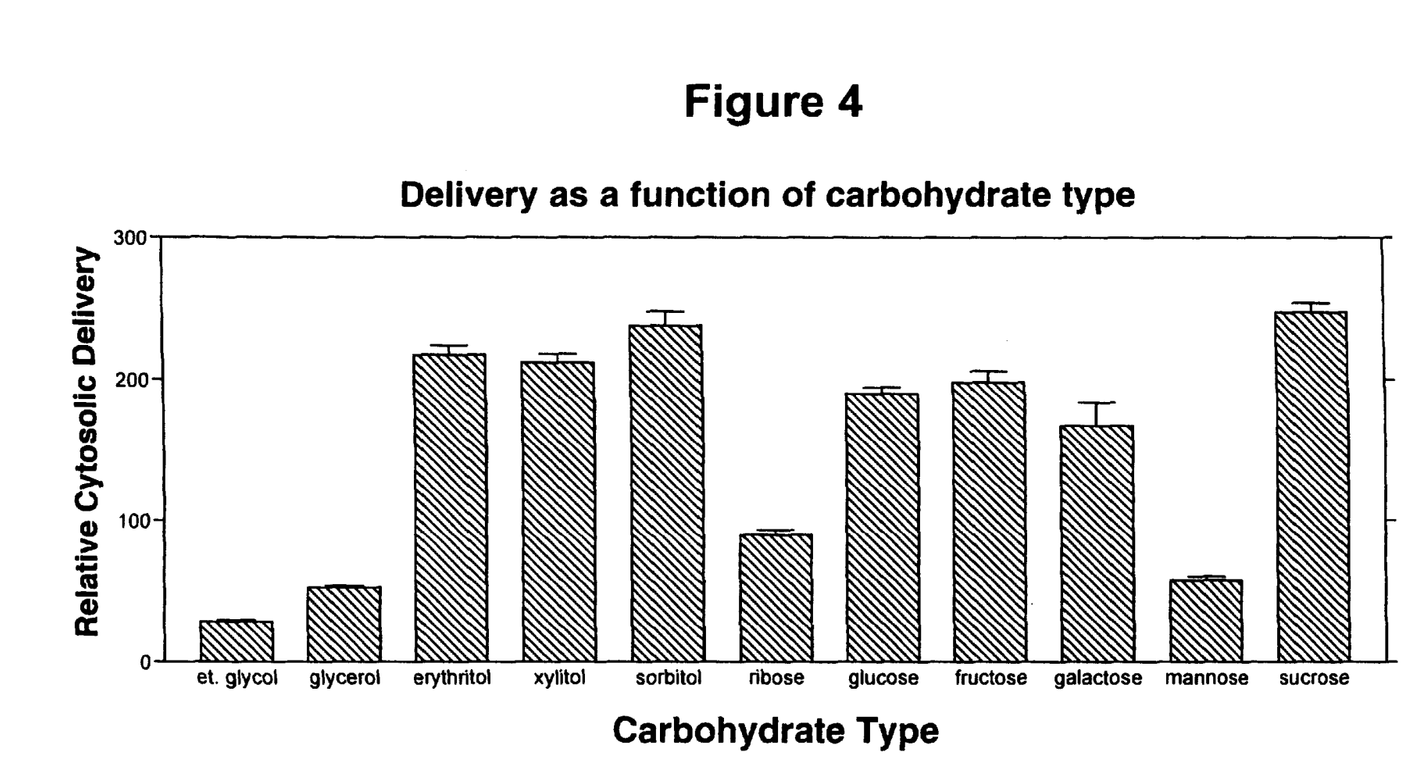
FIG. 4 is a graph showing relative cytosolic delivery as a function of the carbohydrate species.

In regard to representative carbohydrates which satisfy both the membrane-impermeable and water-soluble requirements, experimental results graphed in FIG. 4 indicate that simple non-sugar carbohydrates, such as erythritol (tetra-alcohol), xylitol (penta-alcohol), and sorbitol (hexa-alcohol), and monosaccharides, such as ribose, glucose, fructose, and galactose, as well as water-soluble disaccharides, such as sucrose, are effective for osmotic delivery of substances into the cytosol of cells, with sorbitol and sucrose being particularly effective.

Additional carbohydrate components suitable for osmotic delivery of substances into the cytosol of cells can readily be identified by assessing prospective carbohydrates using the procedure detailed in Example 2.

Accordingly, the carbohydrate component of the osmotic delivery composition of the invention, hereafter designated the "Carbohydrate Component", is selected from those carbohydrates which are both membrane impermeable and water soluble, as per the specifications above.

Osmotic Delivery Composition:

Based on studies of both the PEG Component and the Carbohydrate Component, an improved osmotic delivery composition has been devised which is generally more effective than prior art osmotic delivery compositions—which all contain PEG-1000 or PEG-1500. This improved osmotic delivery composition of the instant invention, hereafter designated the "Osmotic Delivery Composition", comprises:

a PEG Component having a designated molecular weight value in the range between about 300 daltons and about 900 daltons; and, a Carbohydrate Component which is water-soluble and membrane-impermeable.

Figure 5:
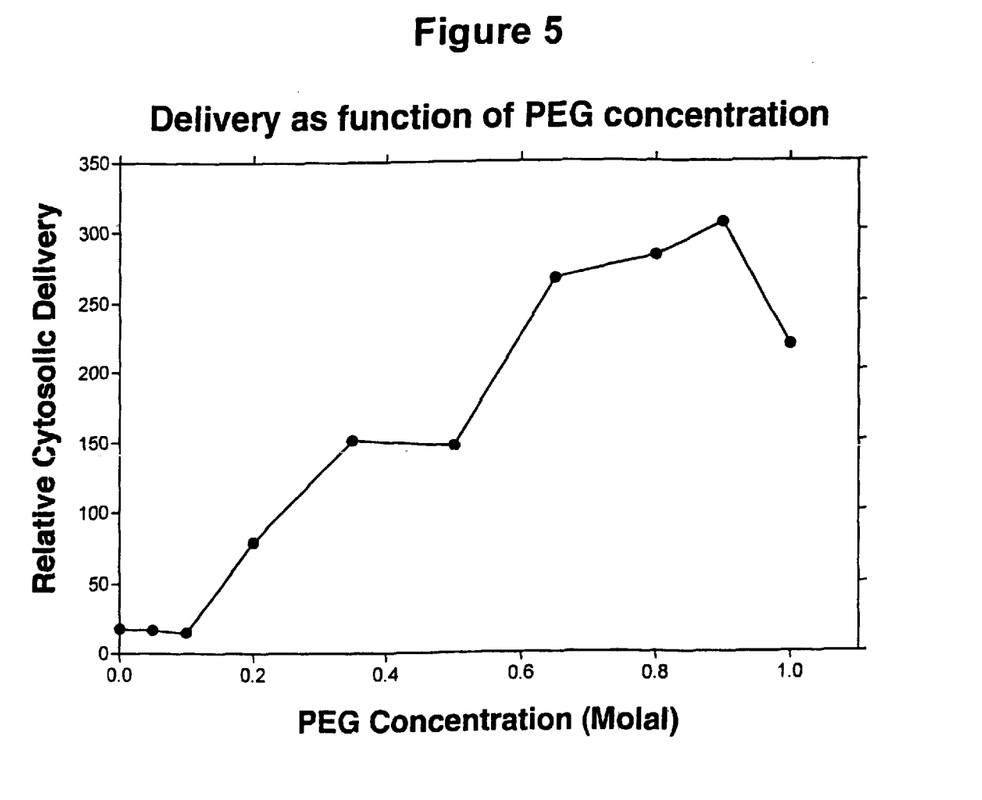
FIG. 5 is a graph showing relative cytosolic delivery as a function of the concentration of the PEG Component.
Figure 6:
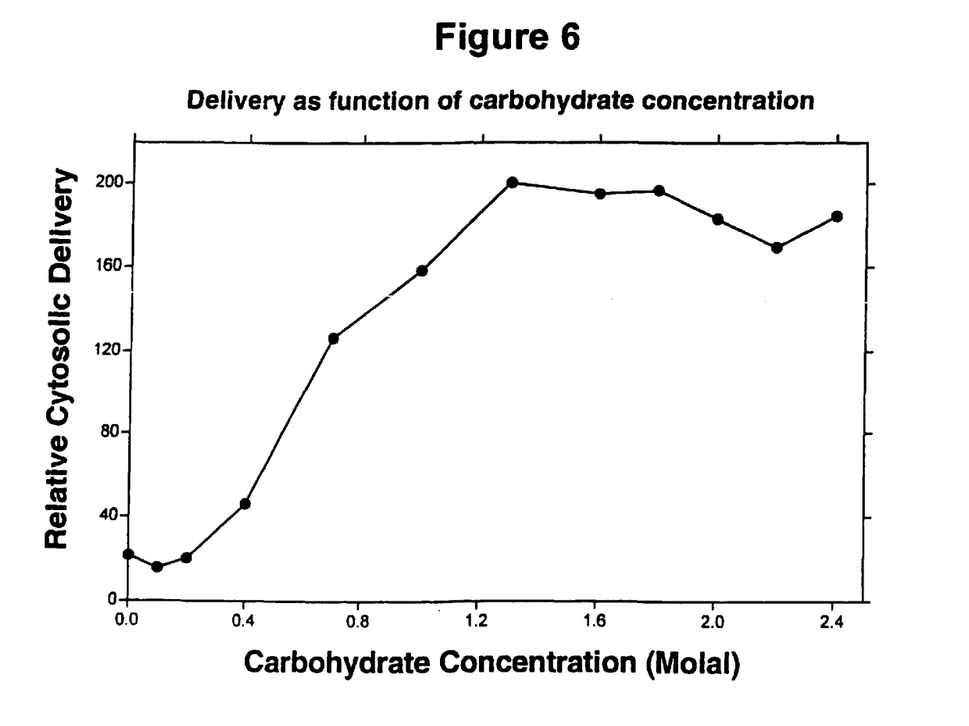
FIG. 6 is a graph showing relative cytosolic delivery as a function of the concentration of the Carbohydrate Component.

Based on studies detailed in Examples 3 and 4, with results shown in FIGS. 5 and 6, the preferred mole ratio of the PEG Component to the Carbohydrate Component of the Osmotic Delivery Composition is such that upon dissolution of the Osmotic Delivery Composition of the instant invention in an aqueous medium, the resulting concentration of the PEG Component is in the range of about 0.2 Moial to about 1.0 Molal and the concentration of the Carbohydrate component is in the range of about 0.5 Molal to about 2.5 Molal if water is the aqueous medium, or in the range of about 0.2 Molal to about 2.2 Molal if normal-saline or cell culture medium is the aqueous medium.

To achieve these respective concentrations the PEG Component of the Osmotic Delivery Composition comprises between about 8 Mole % and about 83 Mole %, and the Carbohydrate Component compises between about 17 Mole % and about 92 Mole %.

A preferred Osmotic Delivery Composition has a PEG Component comprising between about 15 Mole % and about 50 Mole % and a Carbohydrate Component comprising between about 50 Mole % and about 85 Mole %.

A particularly preferred Osmotic Delivery Composition comprises about 34 Mole % PEG-600 and about 66 Mole % sorbitol.

Osmotic Delivery Solution:

Before using the Osmotic Delivery Composition it must be dissolved in an aqueous medium. One has great latitude in selecting this aqueous medium, with the following giving good results: water; normal saline (0.15 N NaCl); and, commercially-available cell culture media, with or without added serum, such as can be purchased from Sigma Chemical Co., St. Louis, Mo.

In regard to the concentration of the PEG Component in the aqueous solution of the Osmotic Delivery Composition, Example 3 describes an experiment to assess the range of concentrations of the PEG Component which affords effective cytosolic delivery of the co-dissolved one or more substances to be delivered into the cytosol of cells. The results of this study, graphed in FIG. 5, show that the PEG Component is effective at concentrations ranging from about 0.2 Molal to about 1.0 Molal.

In regard to the concentration of the Carbohydrate Component in the aqueous solution of the Osmotic Delivery Composition, Example 4 describes an experiment to assess the range of concentrations of the Carbohydrate Component which affords effective cytosolic delivery of the co-dissolved one or more substances to be delivered into the cytosol of cells. The results of this study, graphed in FIG. 6, show that when the aqueous medium is water the Carbohydrate Component is effective at concentrations ranging from about 0.5 Molal to about 2.5 Molal. When the aqueous medium is normal-saline or cell culture medium (which contributes about 0.3 to the osmolality), it has been found that the Carbohydrate Component is effective at concentrations ranging from about 0.2 Molal to about 2.2 Molal.

This relationship between the identity of the aqueous medium and the concentration of the Carbohydrate Component effective for cytosolic delivery is illustrated in Table 1.

TABLE 1

Range of effective concentrations of components of Osmotic Delivery Composition in aqueous medium

| | |
|---|---|
| PEG component: | 0.2 Molal to 1.0 Molal |
| Carbohydrate component: | |
| in saline or cell culture med. | 0.2 Molal to 2.2 Molal |
| in H$_2$O | 0.5 Molal to 2.5 Molal |

Based on the results from the studies detailed in Examples 3 and 4, an improved osmotic delivery solution has been devised which is generally more effective than prior art osmotic delivery solutions. This improved solution of the instant invention, hereafter designated the "Osmotic Delivery Solution", is an aqueous solution comprising:

a PEG Component in the concentration range between about 0.2 Molal and about 1.0 Molal; and, a Carbohydrate Component in the concentration range between about 0.2 Molal and about 2.5 Molal.

Substances to be Delivered Into the Cytosol of Cells:

Substances which can be delivered into the cytosol of cells with the Osmotic Delivery Composition and the Osmotic Delivery Solution of the instant invention include substances used in a variety of research endeavors, as well as drugs used in extracorporal therapy. In this invention, any and all substances which may be endocytosed into cells are encompassed in the term "Desired Substances". Particular Desired Substances deliverable by the instant invention include reporter-tagged molecules and complexes, drugs, antisense and antigene oligos, RNAs, DNAs, peptides, proteins, carbohydrates, and combinations thereof. Of particular value is the delivery of antisense oligos, and particularly Morpholino antisense oligos described by Summerton & Weller (*Antisense & Nucleic Acid Drug Dev.* 7:187 (1997)). Such antisense oligos constitute tools for studying the function and control of genes. Antisense oligos are also useful for target validation in drug development programs. Antisense oligos may also be used in extracorporal therapy for blocking the activity of one or more genes responsible for pathological processes in the treated cells. In this invention extracorporal therapy refers to removing cells from an individual, treating those cells outside the body, and then reintroducing the treated cells into the same individual or into a different individual, as described in greater detail in Example 8.

Osmotic Delivery Solution With Desired Substances:

In this invention, an Osmotic Delivery Solution which also includes one or more Desired Substances to be delivered into the cytosol of cells is designated the "Osmotic Delivery Solution With Desired Substances" of the instant invention.

Osmotic Delivery Method:

Most prior-art osmotic delivery methods entail sequential treatment of the cells with three different solutions (Okada & Rechsteiner, 1982; McElligott & Dice, 1984; Rechsteiner, 1987; Lee et al., 1993; BioProbes, 1998). Such three-solution delivery methods generally include the steps:

1) contacting the cells with a hypertonic solution containing poly(ethylene glycol)-1000 or -1500, sucrose, and the substance to be delivered into the cytosol of the cells, to load said substance into the endosomes of the cells;
2) removing the hypertonic solution from the cells;
3) contacting the cells with a hypotonic solution to effect release of said substance from the endosomes into the cytosol of the cells;
4) removing the hypotonic solution from the cells; and,
5) adding isotonic cell culture medium to the cells to return the cells to their normal metabolic state.

Exposure of the cells to the hypotonic solution can cause loss of cell viability, with the amount of viability loss being dependent on experimental technique and time of exposure to the hypotonic solution.

In experiments with the Osmotic Delivery Solution of the instant invention it was surprisingly discovered that effective delivery into the cytosol could be achieved without using the hypotonic solution—thereby avoiding viability losses incurred during exposure to hypotonic solution. This finding led to the development of the two-solution osmotic delivery method of the instant invention, hereafter designated the "Osmotic Delivery Method", which affords more delivery, greater simplicity, and reduced cell viability losses relative to the three-solution prior-art osmotic delivery method. This improved Osmotic Delivery Method utilizes only two solutions and requires only two steps, those being:

1. contacting the cells with Osmotic Delivery Solution With Desired Substances; and,
2. adding Cell Culture Medium (defined infra), which serves to: release the Desired Substances from the endosomes into the cytosol of the cells; dilute the Osmotic Delivery Solution to a level where it has little or no detrimental effect on the cells; and, return the cells to their normal metabolic state.

Below, the sequences of preferred steps are compared between the typical prior-art three-solution osmotic delivery method (Rechsleiner, 1987) and the two-solution Osmotic Delivery Method of the instant invention.

| | three-solution prior art method | two-solution method of invention |
|---|---|---|
| 1. | Add 1 volume of hypertonic PEG-1000/sucrose solution to cells for about 10 minutes | Add 1 volume of hypertonic Osmotic Delivery Solution to cells for about 8 to 25 minutes |
| 2. | Remove hypertonic solution from cells | Add about 5 to 25 volumes of isotonic Cell Culture Medium |
| 3. | Wash cells with 15 to 25 volumes of hypotonic medium | |

| three-solution prior art method | two-solution method of invention |
|---|---|
| 4. Repeat cell wash with 15 to 25 volumes of hypotonic medium | |
| 5. Incubate cells for 2 minutes in hypotonic medium | |
| 6. Remove hypotonic medium from cells | |
| 7. Add isotonic cell culture medium to cells | |

In the prior-art three-solution method losses in cell viability are commonly seen to occur in steps 3 through 6 while the cells are exposed to hypotonic solution. It was found that in osmotic delivery with the two-solution Osmotic Delivery Method of the instant invention such viability losses are generally prevented.

While the prior-art three-solution method and the instant two-solution Osmotic Delivery Method both achieve cytosolic delivery, the Osmotic Delivery Method of the instant invention provides the following advantages over the prior-art three-solution method:

- The two-solution Osmotic Delivery Method achieves greater delivery due to a more effective PEG Component.
- The two-solution Osmotic Delivery Method is easier and more convenient to carry out, particularly when multiple samples of adherent cells or when non-adherent cells are to be treated.
- The two-solution Osmotic Delivery Method gives more consistent delivery when multiple cell samples are treated.
- When non-adherent cells are treated by the prior-art three-solution method multiple centrifugations are required. In the two-solution Osmotic Delivery Method no centrifugations are required. This affords a great saving in effort in cases where multiple samples are to be treated.
- The two-solution Osmotic Delivery Method of the instant invention is of particular benefit for extracorporal therapeutic treatments, as described in Example 8, where simplicity of procedure, maintenance of cell viability, and a modest final volume of treated cell suspension for introduction into the patient are of prime importance.

Delivery Time:

In regard to the length of time the cells should be exposed to the Osmotic Delivery Solution With Desired Substances, Example 5 details an experiment where cytosolic delivery was assessed as a function of the time the cells were exposed to the Osmotic Delivery Solution With Desired Substances before addition of cell culture medium. The results, shown in FIG. 7, demonstrate that some delivery occurs with an exposure of just 1 minute. However, exposure of the cells to the Osmotic Delivery Solution With Substances for a period of time in the range between about 8 minutes and about 25 minutes is preferred, with about 15 minutes being most preferred.

Thus, a preferred embodiment of the first step of the Osmotic Delivery Method comprises:

contacting the cells with Osmotic Delivery Solution With Desired Substances for a period of time between about 8 minutes and about 25 minutes.

Figure 7:
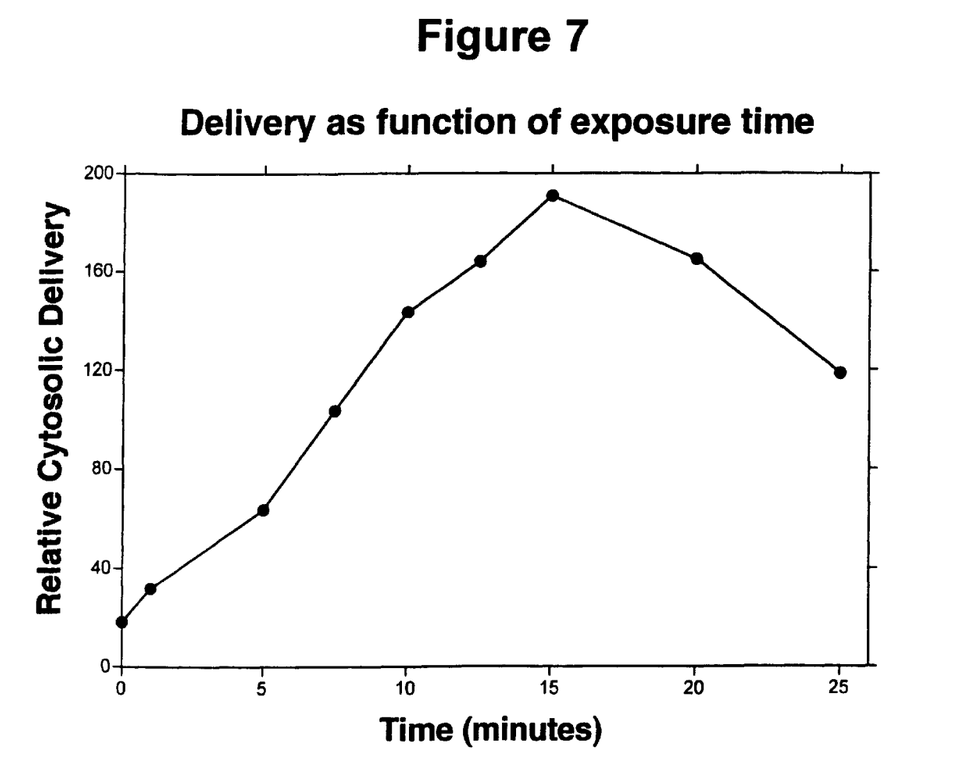
FIG. 7 is a graph showing relative cytosolic delivery as a function of the time of exposure to Osmotic Delivery Solution.

As can be seen in the graph of FIG. 7, contacting the cells with Osmotic Delivery Solution With Desired Substances for a period of time between about 10 minutes and about 20 minutes is particularly preferred, with 15 minutes being the most preferred.

Cell Culture Medium:

In the Osmotic Delivery Method of the instant invention isotonic or near-isotonic cell culture medium is added after the cells have been exposed to the Osmotic Delivery Solution With Desired Substances for a suitable period of time. This cell culture medium serves to: a) effect release of Desired Substances from endosomes to the cytosol of the cells; b) dilute the Osmotic Delivery Solution to a level where it has little or no detrimental effect on the cells; and, c) return the cells to their normal metabolic state and provide needed nutrients, growth factors, and buffering capacity.

In principle, an acceptable osmolality for the mixture resulting from solutions added in step 1 and step 2 of the Osmotic Delivery Method can be obtained simply by adding in step 2 a suitable volume of water to afford a final osmolality of the mixture in the range between about 0.3 and about 0.5. However, while this does afford the desired release of endosomal contents into the cytosol of cells, it fails to effectively achieve the other requirements for the solution added in step 2 of the method—those being: a) to dilute the Osmotic Delivery Solution to a level where it has little or no detrimental effect on the cells; and, b) to return the cells to their normal metabolic state and provide needed nutrients, growth factors, and buffering capacity.

It has been found that adding a suitable volume of isotonic or near-isotonic cell culture medium, hereafter designated the "Cell Culture Medium", in step 2 of the Osmotic Delivery Method best achieves the dual objectives of diluting the Osmotic Delivery Solution and returning the cells to their normal metabolic state. Commercially-available cell culture media, such as are available from Sigma Chemical Co., St. Louis, Mo. and other biological supply companies, are the preferred compositions for the Cell Culture Medium component of the Osmotic Delivery Method of the invention because of the simplicity and versatility this affords.

Example 6 describes an investigation of how to best achieve the dual objectives in step 2 of the Osmotic Delivery Method of diluting the Osmotic Delivery Solution and returning the cells to their normal metabolic state. This experiment entailed assessing the effectiveness of cytosolic delivery as a function of the relative volume of Cell Culture Medium added in step 2 of the Osmotic Delivery Method. From these results, plotted in FIG. 8, and from other experimental results it was concluded that at least about 5 volumes of Cell Culture Medium should be added in step 2 of the Osmotic Delivery Method in order to avoid undue metabolic stress on the cells. Further, it has been found that above a certain volume cytosolic delivery efficiency drops off with increasing volume of Cell Culture Medium added in step 2. This decreasing efficiency, plus ease of use considerations, led to selection of about 25 volumes of Cell Culture Medium as about the practical upper limit for the volume of Cell Culture Medium to be added in step 2 of the Osmotic Delivery Method of the instant invention.

Thus, a preferred embodiment of the second step of the Osmotic Delivery Method comprises:

adding between about 5 and about 25 volumes of Cell Culture Medium in step 2, relative to one volume of Osmotic Delivery Solution With Desired Substances added in step 1.

Figure 8:
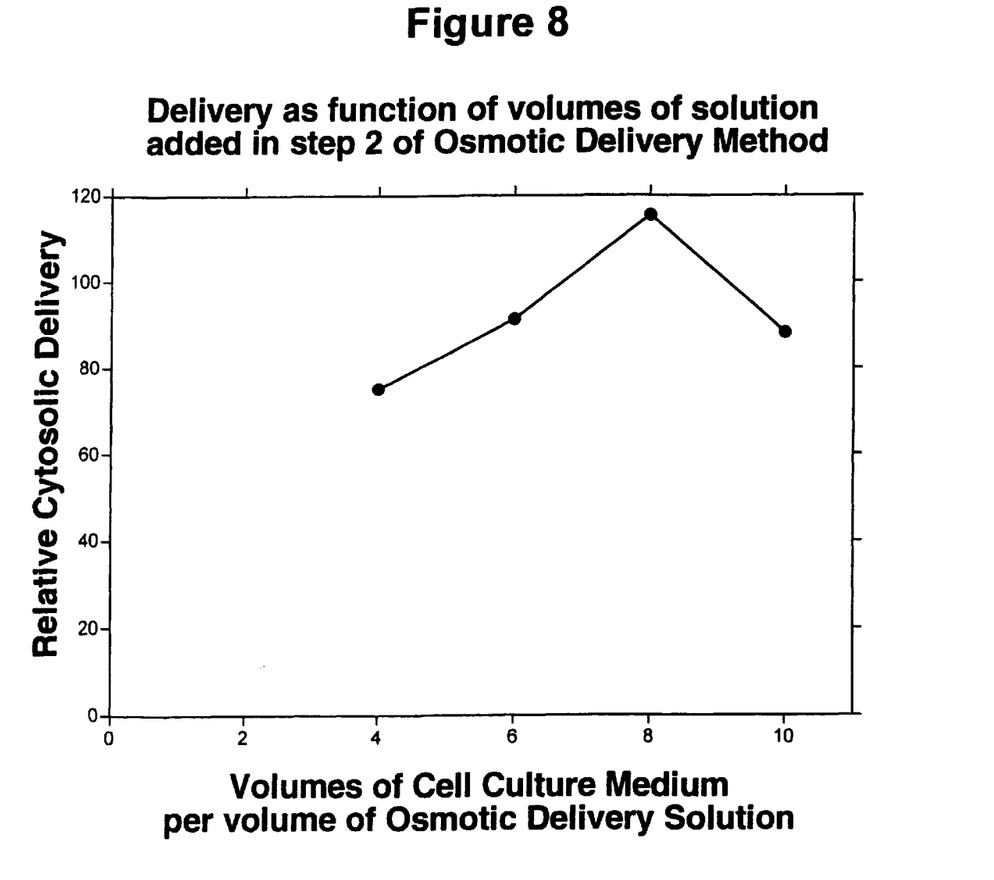
FIG. 8 is a graph showing relative cytosolic delivery as a function of the relative volume of Cell Culture Medium.

It can be inferred from the graph of FIG. 8 that in step 2 addition of between about 6 and about 12 volumes of Cell Culture Medium, relative to the volume of Osmotic Delivery Solution With Desired Substances added in step 1, is particularly preferred.

Preferred Composition and Method:

Example 7 describes a representative application which illustrates the preparation of an Osmotic Delivery Composition, an Osmotic Delivery Solution, an Osmotic Delivery Solution With Desired Substances, and Cell Culture Medium, and their use in the Osmotic Delivery Method of the instant invention.

Extracorporal Therapy:

Example 8 describes the preparation of an Osmotic Delivery Composition, an Osmotic Delivery Solution, an Osmotic Delivery Solution With Desired Substances, and Cell Culture Medium, and their use in the Osmotic Delivery Method of the instant invention for extracorporal therapy.

EXAMPLES

Example 1

Assessment of Cytosolic Delivery as a Function of PEG Molecular Weight

A. Basis of Test System

To assess for cytosolic delivery cells were used that were stably transfected with a plasmid (pLUC/705) which encodes a pre-messenger RNA construct comprising a mutant human beta-globin leader sequence joined to the amino acid coding sequence of firefly luciferase (Kang et al., Biochemistry 37:6235 (1998)). The mutant leader sequence contains a mutation at base 705 in intron 2 that generates a new splice site which, in combination with a cryptic upstream splice site, results in a portion of intron 2 being retained in the spliced mRNA, where said portion of intron 2 contains a termination codon. As a consequence, the resultant mutant spliced mRNA is not translated and so fails to produce luciferase.

It has been demonstrated previously that Morpholino antisense oligos (Summerton & Weller, *Antisense & Nucleic Acid Drug Dev.* 7:187 (1997)) enter unperturbed cultured animal cells via endocytosis, and remain sequestered in the endosome/lysosome compartment indefinitely, with little or none entering the cytosol (Summerton et al., *Antisense & Nuc. Acid Drug Dev.* 7:63 (1997)). However, when a Morpholino antisense oligo targeted against the mutation at base 705 of intron 2 is directly delivered into the cytosol/nuclear compartment of cells via scrape-loading (Partridge et al., *Antisense & Nuc. Acid Drug Dev.* 6:169 (1996)), said oligo has been shown to be highly effective in blocking the mutant splice site, thereby correcting the splicing error. This, in turn, generates a correctly-spliced globin/luciferase mRNA that is translated to generate luciferase (Morcos, *Methods in Enzymology*, in press (1999)). This positive test system is particularly attractive for assessing the combination of cytosolic delivery and cell viability because luciferase (readily assessed by adding luciferol and quantitating the resulting light emission in a luminometer) is only generated when: a) cytosolic delivery of the antisense oligo is achieved; and, b) the cells remain metabolically active and capable of transcription, nuclear processing, and translation.

B. Materials

Sucrose was purchased from Aldrich Chemical Co., Milwaukee, Wis. Poly(ethylene glycol) (commonly referred to as PEG) preparations having designated molecular weights ranging from 200 to 2000 were purchased from Aldrich Chem. Co., Milwaukee, Wis. An additional preparation of poly(ethylene glycol)-600 was purchased from Arcos/Fisher Scientific, Pittsburgh, Pa. Cell culture medium DMEM/F12 with 10% FBS (Catalog #10-092-CV) was purchased from Mediatech, Herndon, Va. The 25-mer splice-corrector Morpholino antisense oligo, having the sequence: 5'-CCTCTTACCTCAGTTACAATTTATA-3', was prepared by GENE TOOLS, LLC, Corvallis, Oreg.

C. Cells

HeLa cells stably transfected with plasmid pLUC/705, coding for the above-described mutant globin/luciferase pre-mRNA construct, were provided by GENE TOOLS, LLC. The cells were cultured in DMEM/F12 with 10% FBS medium.

D. Luciferase and Protein Assays

Firefly luciferase in cell lysates was assessed as described in Promega publication # TB101 using the Promega assay system, Catalog # E1500 (Promega Corp., Madison, Wis.). Protein from the cell lysates was quantitated using the BioRad protein assay reagent, Catalog #500-0006 (BioRad Corp., Hercules, Calif.).

E. Assessment of Cytosolic Delivery

Approximately $2 \times 10^5$ HeLa cells stably transfected with pLUC/705 were seeded into each well of a 24-well plate (1.6 cm well diameter) and incubated at 37° C. for 16 hours.

i) Osmotic Delivery Compositions were prepared by adding 0.4 g (1.17 milliMole) of sucrose to 0.3 g of each of the poly(ethylene glycol) preparations of the following designated molecular weight values: 300, 400, 600, and 900. Related compositions were prepared by adding 0.4 g (1.17 milliMole) of sucrose to 0.3 g of each of the poly(ethylene glycol) preparations of the following designated molecular weight values: 200, 1000, 1500, and 2000.

ii) Osmotic Delivery Solutions and related solutions were formed by adding 1 ml of water to each of the above compositions and agitating until dissolution was complete.

iii) Osmotic Delivery Solutions With Desired Substances and related solutions with Desired Substances were formed by adding 20 microLiters of an aqueous 500 microMolar solution of splice-corrector Morpholino antisense oligo to each of the above Osmotic Delivery Solutions and related solutions.

iv) The Morpholino antisense oligo (Desired Substances) was introduced into the cytosol of the cells by the Osmotic Delivery Method and related method by:

a) aspirating cell culture medium from the adherent cells in each well of the plate;

b) adding to each well 0.15 ml of Osmotic Delivery Solution With Desired Substances or a related solution with Desired Substances and swirling briefly;

c) incubating the culture plate at 37° C. for 10 minutes, with brief swirling at 5 minutes; and, d) adding to each well 1.5 ml of Near-Isotonic Cell Culture Medium (DMDM/F12 with 10% FBS).

The amount of antisense oligo delivered into the cytosol of the cells by this procedure was determined by incubating the cells in the culture plate at 37° C. for an additional 16 hours, after which the cells in each well were lysed and each lysate assayed for both luciferase and protein by methods described in section D of this Example. The relative luciferase values, which are proportional to the amount of antisense oligo delivered into the cytosol, were calculated by dividing the light intensity by the quantity of protein determined for the lysate from each sample well. Dividing the light intensity by the protein value affords luciferase values normalized to cell number. This normalization process factors out variations in well-to-well cell plating densities, as well as variations in cell numbers due to other factors.

The results, graphed in FIG. 3, indicate that under the conditions of this experiment PEGs in the molecular weight range between about 300 and about 900 daltons provide the best cytosolic delivery, with PEG-600 being particularly effective.

Example 2

Assessment of Cytosolic Delivery as a Function of Carbohydrate Species

Cytosolic delivery of a splice-corrector Morpholino antisense oligo was assessed as in Example 1, with the following changes:

i) Osmotic Delivery Compositions and related compositions were prepared by adding 1.17 milliMole of respective carbohydrate to 0.3 g (approx. 0.5 milliMole) of PEG-600; where the carbohydrates included: the non-sugar poly-alcohols ethylene glycol, glycerol, meso-erythritol, xylitol, and sorbitol; the monosaccharides ribose, glucose, fructose, galactose, and mannose; and the disaccharide sucrose. These carbohydrates were purchased from Aldrich Chem. Co., Milwaukee, Wis.

Osmotic Delivery Solutions and related solutions, and Osmotic Delivery Solutions With Desired Substances and related solutions with Desired Substances were prepared as in Example 1 using the above Osmotic Delivery Compositions and related compositions.

The Morpholino antisense oligo was introduced into the cells by the Osmotic Delivery Method and related method as in Example 1. The amount of antisense oligo delivered into the cytosol of said cells was calculated based on relative luciferase values determined as in Example 1. The results, graphed in FIG. 4, indicate that under the conditions of this experiment the tested carbohydrates having greater than three hydroxyls provide effective cytosolic delivery, with sucrose and sorbitol being particularly effective.

Example 3

Assessment of Cytosolic Delivery as a Function of the Concentration of the PEG Component Cytosolic delivery of a splice-corrector Morpholino antisense oligo was assessed as in Example 1, with the following changes.

i) Osmotic Delivery Compositions were prepared by adding 1.2 milliMole (0.218 g) of sorbitol to varying portions of PEG-600, said portions including: 0 g, 0.03 g (approx. 0.05 milliMole), 0.06 g (approx. 0.10 milliMole), 0.12 g (approx. 0.20 milliMole), 0.21 g (approx. 0.35 milliMole), 0.30 g (approx. 0.50 milliMole), and 0.39 g (approx. 0.65 milliMole), 0.48 g (approx. 0.80 milliMole), 0.54 g (approx. 0.90 milliMole), and 0.60 g (approx. 1.0 milliMole).

Osmotic Delivery Solutions and Osmotic Delivery Solutions With Desired Substances were prepared as in Example 1 using the above Osmotic Delivery Compositions.

The splice-corrector Morpholino antisense oligo was introduced into the cells by the Osmotic Delivery Method as in Example 1, and the amount of antisense oligo delivered into the cytosol of said cells was also calculated based on relative luciferase values determined as in Example 1.

The results, graphed in FIG. 5, indicate that under the conditions of this experiment the PEG Component at concentrations ranging from about 0.2 Molal to about 1.0 Molal provide effective cytosolic delivery, with about 0.5 Molal to about 0.9 Molal being particularly effective.

Example 4

Assessment of Cytosolic Delivery as a Function of the Concentration of the Carbohydrate Component Cytosolic delivery of a splice-corrector Morpholino antisense oligo was assessed as in Example 1, with the following changes.

i) Osmotic Delivery Compositions were prepared by adding varying portions of sorbitol to 0.3 g (approx. 0.5 milliMole) of PEG-600, where the sorbitol portions included: 0 g, 0.018 g (0.10 milliMole), 0.036 g (0.20 milliMole), 0.073 g (0.40 milliMole), 0.127 g (0.70 milliMole), 0.182 g (1.0 milliMole), and 0.237 g (1.3 milliMole) 0.291 g (1.6 milliMole), 0.328 g (1.8 milliMole), 0.364 g (2.0 milliMole), 0.400 g (2.2 milliMole), and 0.437 g (2.4 milliMole).

Osmotic Delivery Solutions and Osmotic Delivery Solutions With Desired Substances were prepared as in Example 1 using the above Osmotic Delivery Compositions.

The splice-corrector Morpholino antisense oligo was introduced into the cells by the Osmotic Delivery Method as in Example 1, and the amount of antisense oligo delivered into the cytosol of said cells was also calculated based on relative luciferase values determined as in Example 1.

The results, graphed in FIG. 6, indicate that under the conditions of this experiment the Carbohydrate Component at concentrations ranging from about 0.5 Molal to about 2.5 Molal provide effective cytosolic delivery, with concentrations of about 1.0 to about 2.0 being particularly effective. In other experiments where normal saline (contributing 0.3 to the osmolality) was used as the aqueous medium for making the Osmotic Delivery Solution With Desired Substances, the Carbohydrate Component at concentrations ranging from about 0.2 Molal to about 2.2 Molal provided similar cytosolic delivery.

Example 5

Assessment of Cytosolic Delivery as a Function of Time of Exposure to Osmotic Delivery Solution in Step 1 of Osmotic Delivery Method Cytosolic delivery as a function of the duration of the first step of the Osmotic Delivery Method was assessed as in Example 1, excepting:

a) the Osmotic Delivery Composition comprised 0.212 g (1.17 milliMole) of sorbitol and 0.3 g (approx. 0.5 milliMole) of PEG-600; and, b) in the Osmotic Delivery Method the cells were exposed to the Osmotic Delivery Solution With Desired Substances for varying times, including: 1 minute, 5 minutes, 7.5 minutes, 10 minutes, 12.5 minutes, 15 minutes, 20 minutes, and 25 minutes.

The results, graphed in FIG. 7, indicate that under the conditions of this experiment effective cytosolic delivery is achieved with exposure times ranging from about 8 minutes to about 25 minutes, with particularly good delivery being achieved with an exposure time of 15 minutes.

Example 6

Assessment of Cytosolic Delivery as a Function of Volume of Cell Culture Medium Added in Step 2 of Osmotic Delivery Method Cytosolic delivery as a function of the volume of Cell Culture Medium added in step 2 of the Osmotic Delivery Method was assessed as in Example 1, excepting:

a) the Osmotic Delivery Solution comprised 0.212 g (1.17 milliMole) of sorbitol and 0.3 g (approx. 0.5 milliMole) of PEG-600 in 1 ml of water;

b) in the first step of the Osmotic Delivery Method the cells were contacted with 0.15 ml of the Osmotic Delivery Solution With Desired Substances for a period of 15 minutes; and, c) in the second step of the Osmotic Delivery Method varying volumes of Cell Culture Medium (DMEM/F12 with 10% FBS) were added, including: 0.6 ml, 0.9 ml, 1.2 ml, and 1.5 ml, corresponding to 4 volumes, 6 volumes, 8 volumes, and 10 volumes, respectively, with respect to the 0.15 ml volume of Osmotic Delivery Solution With Desired Substances added in step 1 of the Osmotic Delivery Method.

The results, graphed in FIG. 8, indicate that under the conditions of this experiment at least about 5 volumes of Near-Isotonic Cell Culture Medium is required to provide effective cytosolic delivery, with about 6 to about 10 volumes affording particularly good delivery.

Example 7

Preferred Osmotic Delivery Composition and Osmotic Delivery Method

Cytosolic delivery of a splice-corrector Morpholino antisense oligo was carried out as described below to demonstrate a preferred composition, preferred solutions, and a preferred method of the instant invention.

Osmotic Delivery Composition was prepared by mixing 1.3 milliMole of sorbitol and 0.4 g of PEG-600.

Osmotic Delivery Solution was prepared by adding 0.98 ml of water to the above composition.

Osmotic Delivery Solution With Desired Substances was prepared by adding to this Osmotic Delivery Solution 20 microLiter of a 500 microMolar aqueous solution of the splice-corrector Morpholino antisense oligo of Example 1.

A. Adherent Cells

HeLa cells were plated in the wells of a 24-well plate as in Example 1. Sixteen hours later cell culture medium was removed from the wells and 0.13 ml of Osmotic Delivery Solution With Substances was added to each well and the plate swirled briefly and then placed in a 37° C. incubator. After 7 minutes the plate was again swirled briefly and replaced in the incubator. Fifteen minutes after addition of the Osmotic Delivery Solution With Desired Substances 1.0 ml of Cell Culture Medium (DMEM/F12 with 10% FBS) was added to each well and the plate swirled thoroughly and replaced in a 37° C. incubator.

Sixteen hours later cytosolic delivery of the Morpholino antisense oligo was confirmed by the presence of substantial amounts of luciferase in the cells, quantitated as in Example 1.

B. Non-Adherent Cells

Approximately $10^6$ Hela cells stably transfected with the pLUC/705 plasmid were seeded into each 3.5 cm diameter well of a 6-well plate and allowed to grow overnight. The next day medium was removed and the cells were released from all 6 wells of the plate with 0.25% trypsin-EDTA medium. The cells were pooled in a 15 ml centrifuge tube and pelleted by brief centrifugation. The trypsin-EDTA medium was aspirated off from the cell pellet and the cells resuspended in 2.4 ml of DMEM/F12 medium. 0.1 ml portions of this cell suspension were transferred to 1.5 ml microfuge tubes and centrifuged briefly to pellet the cells. The medium was aspirated off and 0.13 ml of the Osmotic Delivery Solution With Desired Substances added to each cell pellet. The cells were resuspended by brief agitation and then incubated for 15 minutes at 37° C. Next, 1.0 ml of Cell Culture Medium (DMEM/F12 with 10% FBS) was added to each tube, the tube agitated briefly, and then the cell suspension from each tube was transferred to a 1.6 cm diameter well of a 24-well plate and the plate placed in a 37° C. incubator.

Sixteen hours later, cytosolic delivery of the Morpholino antisense oligo was confirmed by the presence of substantial amounts of luciferase in the cells, quantitated as in Example 1.

Example 8

Cytosolic Delivery by Osmotic Delivery Method in Extracorporal Therapy

Autologous extracorporal therapy is a process where: a) cells are removed from a patient (cell donor); b) the cells are treated to block the activity of one or more genes responsible for pathological processes occurring within those cells, or to selectively kill only the diseased cells; and; c) the treated cells are reintroduced into that patient (cell recipient). Typically while said cells are out of the patient, the patient is treated by radiotherapy and/or chemotherapy sufficient to kill all of the cells remaining within the patient of the cell type (commonly bone marrow cells) involved in the pathological process affecting the patient.

A related heterologous extracorporal therapy can also be carried out where normal cells from a donor (cell donor) are treated (such as with biologically-stable Morpholino antisense oligos) to render the cells immune to some pathological process (such as infection with the HIV virus). The treated cells are then introduced into a tissue-matched patient (cell recipient) suffering from said pathological process.

Following are procedures which can be used for such extracorporal therapies. Bone marrow cells are obtained from the iliac crest of the cell donor by methods known in the art (Schwartz, Int. *J. Cell Cloning* 7:360 (1989)). Cells withdrawn from the marrow of the bone are separated on a Ficoll-sodium diatrizoate gradient (LSM; OrganonTeknika Corp, Durham, N.C.), and those cells with a density of about 1.077 g/ml are isolated and washed three times with DMEM cell culture medium containing 10% heat-inactivated FBS. The cells are pelleted briefly in 50 ml conical centrifuge tubes and the supernatant aspirated off. Filter-sterilized or autoclaved Osmotic Delivery Solution With Desired Substances (where said Desired Substances are suitable for treating said cells) having a volume of about 10 times that of the cell pellet, is added to the cells and the tube agitated briefly to resuspend the cells and then incubated at 37° C. After 15 minutes 8 volumes (relative to the volume of added Osmotic Delivery Solution With Substances) of Cell Culture Medium (DMEM cell culture medium) is added to the cell suspension and the preparation is incubated in cell culture flasks for 2 hours at 370° C. with 5% $CO_2$. This suspension of treated cells is then introduced into the cell recipient.

What is claimed is:

1. A method of extracorporal therapy comprising:
    a) removing cells from an individual;
    b) introducing desired substances into the cytosol of said cells by an osmotic delivery method which includes contacting the cells with an osmotic delivery solution of
        a poly(ethylene glycol) component having a designated molecular weight in the range between about 300 and about 900 daltons and
        a carbohydrate component which is water-soluble and membrane-impermeable
        said components dissolved in aqueous medium to give a solution having a polyethylene glycol) concentration in the range between about 0.2 Molal and about 1.0 Molal, and a carbohydrate concentration in the range between about 0.2 Molal and about 2.5 Molal, and said solution further including one or more desired substances to be delivered into the cytosol of the cells;

followed by, adding cell culture medium;

and then, c) introducing said treated cells into the same individual or a different individual.

2. The method of extracorporal therapy of claim 1 wherein one or more of the desired substances to be delivered into the cytosol of cells include at least one antisense oligo.

3. The method of extracorporal therapy of claim 2 wherein at least one desired substance is a morpholino antisense oligo.

4. The method of claim 1 wherein the poly(ethylene glycol) component is PEG-600 with a molecular weight of about 600 daltons.

5. The method of claim 1 wherein the carbohydrate component is sorbitol.

6. The method of claim 4 wherein the PEG 600 is present in a concentration of about 0.4 gram per milliliter of water.

7. The method of claim 5 wherein the sorbitol is present in a concentration of about 1.3 molal.

* * * * *